United States Patent
Haeggström et al.

(12)

(10) Patent No.: US 10,765,558 B2
(45) Date of Patent: Sep. 8, 2020

(54) METHOD AND ARRANGEMENT FOR EYE MEASUREMENTS

(71) Applicant: PHOTONO OY, Helsinki (FI)

(72) Inventors: Edward Haeggström, Helsinki (FI); Ari Salmi, Helsinki (FI); Ivan Kassamakov, Helsinki (FI); Heikki Nieminen, Helsinki (FI); Timo Rauhala, Helsinki (FI); Kalle Hanhijärvi, Helsinki (FI); Antti Kontiola, Helsinki (FI)

(73) Assignee: PHOTONO OY, Helsinki (FI)

( * ) Notice: Subject to any disclaimer, the term of this patent is extended or adjusted under 35 U.S.C. 154(b) by 54 days.

(21) Appl. No.: 15/911,867

(22) Filed: Mar. 5, 2018

(65) Prior Publication Data
US 2018/0193194 A1    Jul. 12, 2018

Related U.S. Application Data

(63) Continuation of application No. PCT/FI2015/050579, filed on Sep. 3, 2015.

(51) Int. Cl.
*A61F 9/007* (2006.01)
*A61F 9/008* (2006.01)
*A61B 3/16* (2006.01)
*A61B 3/10* (2006.01)

(52) U.S. Cl.
CPC ........ *A61F 9/00781* (2013.01); *A61B 3/1005* (2013.01); *A61B 3/16* (2013.01);
(Continued)

(58) Field of Classification Search
CPC ........ A61F 9/00781; A61F 2009/00872; A61F 9/008
See application file for complete search history.

(56) References Cited

U.S. PATENT DOCUMENTS

| 5,148,807 A | 9/1992 | Hsu |
| 5,251,627 A | 10/1993 | Morris |

(Continued)

FOREIGN PATENT DOCUMENTS

| JP | S57-123797 | 8/1982 |
| JP | H02-121623 | 5/1990 |

(Continued)

OTHER PUBLICATIONS

International Search Report (PCT/ISA/210) dated May 19, 2016, by the Finnish Patent Office as the International Searching Authority for International Application No. PCT/FI2015/050579.

(Continued)

*Primary Examiner* — Jack Dinh
(74) *Attorney, Agent, or Firm* — Nixon & Vanderhye

(57) ABSTRACT

An intraocular pressure measurement arrangement is disclosed for measuring pressure of an eye of a patient. The arrangement can detect at least one of acoustic reflectivity, optical reflectivity, optical path difference, positioning of intraocular pressure measurement arrangement with respect to the eye, orientation of intraocular pressure measurement arrangement with respect to the eye, shape of cornea and corneal thickness. At least one source can produce acoustic, nonlinear acoustic, mechanical or a nonlinear mechanical wave from a distance, coupling to the eye to generate at least one surface wave. Upon triggering data acquisition, at least one surface wave from a distance from the eye can be detected to extract surface wave information with pressure information of the eye being based on the surface wave information.

19 Claims, 12 Drawing Sheets

(52) U.S. Cl.
CPC .............. *A61B 3/165* (2013.01); *A61F 9/008* (2013.01); *A61F 2009/00872* (2013.01)

(56) References Cited

U.S. PATENT DOCUMENTS

| | | | |
|---|---|---|---|
| 6,030,343 | A | 2/2000 | Chechersky et al. |
| 2003/0078486 | A1 | 4/2003 | Klein et al. |
| 2004/0193033 | A1 | 9/2004 | Badehi et al. |
| 2010/0249569 | A1 | 9/2010 | Jinde et al. |

FOREIGN PATENT DOCUMENTS

| | | |
|---|---|---|
| JP | 2005-521450 | 7/2005 |
| RU | 2 471 406 C2 | 1/2013 |
| WO | 93/21820 | 11/1993 |
| WO | WO 2015/132467 A1 | 9/2015 |

OTHER PUBLICATIONS

Written Opinion (PCT/ISA/237) dated May 19, 2016, by the Finnish Patent Office as the International Searching Authority for International Application No. PCT/FI2015/050579.

Shang Wang et al., "A focused air-pulse system for optical-coherence-tomography-based measurements of tissue elasticity", Laser Physics Letters, vol. 10, No. 7, May 20, 2013, 7 pages.

Łukasz Ambroziń et al., "Acoustic micro-tapping for non-contact 4D imaging of tissue elasticity", Scientific Report, Dec. 13, 2016, 11 pages.

Japanese Office Action for Application No. 2018-511734 dated Apr. 9, 2019 with English translation provided.

800         801         802

METHOD AND ARRANGEMENT FOR EYE MEASUREMENTS

RELATED APPLICATION

This application claims priority as a continuation application under 35 U.S.C. § 120 to PCT/FI2015/050579 filed as an International Application on Sep. 3, 2015 designating the U.S., the entire content of which is hereby incorporated by reference in its entirety.

FIELD

Intraocular pressure (IOP) plays a major role in the pathogenesis of open angle glaucoma, one of the leading causes of blindness. There are about 150 million people with glaucoma globally, about half of which are unknowingly affected and without diagnosis. The prevalence of glaucoma increases with aging of the human population and it is expected that this will increase by 30% the number of glaucoma cases during the next decade. The only way to currently treat glaucoma is by lowering the intraocular pressure (IOP).

An IOP measurement is the most practical way of screening open angle glaucoma. However, screening large parts of the population is needed to find undiagnosed cases.

The other type of glaucoma is the narrow angle glaucoma that causes a sudden IOP increase that may cause blindness in a few days. Since one per mille of the population is affected with acute narrow angle closure glaucoma, it is mandatory to diagnose acute glaucoma by measuring IOP in community emergency departments of general medicine. Consequently it would be beneficial if every doctor's office would have an ability to measure IOP.

BACKGROUND INFORMATION

Contact methods (e.g. Goldmann tonometry, Mackay-Marg tonometry) for measuring IOP mostly involve use of an anesthetic to carry out the measurement and are thus impractical for screening large human populations. Also non-contact air impulse tonometers have been on the market for decades. Air impulse tonometers can result in patient discomfort experienced due to an air impulse.

US patent application document US 2010/0249569 A1 presents a non-contact ultrasonic tonometer for IOP measurements, which employs piezo-electric transducers to excite wave signals into the eye. The positions of the transducers have to be exactly measured, which makes the IOP measurement procedure complex and slow. Also temperature variations cause error and uncertainty in the IOP measurement information together with possible errors in position measurements. The eye shape can also introduce bias, i.e. error, into the measurement.

Patent document U.S. Pat. No. 6,030,343 A presents a method that is based on an airborne ultrasonic beam that is reflected from the cornea—the same beam measures and actuates the eye. The actuation is done by a narrow band ultrasonic tone burst, which deforms the cornea, and the system measures the phase shift from the deformed eye.

Patent documents US2004/193033 and U.S. Pat. No. 5,251,627 describe a non-contact measurement method by way of linear excitation (e.g. loudspeakers or ultrasonic transducers).

Known solutions have difficulty providing a convenient and low-cost device for measuring IOP precisely and comfortably for a patient by non-contact measurements.

SUMMARY

An intraocular pressure measurement arrangement is disclosed for measuring eye pressure arrangement comprising: at least one source for producing an excitation pressure pulse formed by nonlinear waves and transmitted by air to generate at least one surface wave for an eye measurement; means for detecting the at least one surface wave at a distance from a surface to extract eye surface wave information; and means for determining the eye pressure based on said surface wave information.

An intraocular pressure measurement method is also disclosed for measuring eye pressure, the method comprising: producing an excitation pressure pulse formed by nonlinear waves and transmitted by air to generate at least one surface wave for an eye measurement; detecting at least one surface wave at a distance from a surface to extract eye surface wave information; and determining the eye pressure based on said surface wave information.

DETAILED DESCRIPTION

Figure 1:
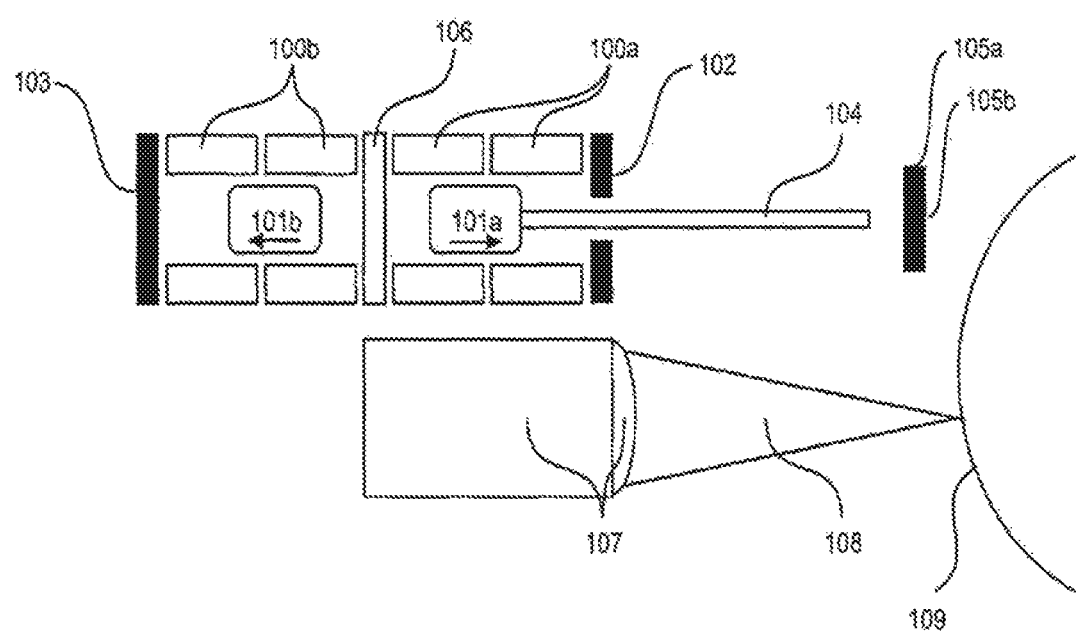
FIG. 1 presents an exemplary embodiment of a measurement arrangement with a solenoid-driven impacting device capable of non-linear wave excitation and optical pickup means.

A contactless, fast and advanced device and method are disclosed to measure IOP without need for anaesthetics. An IOP reading that results in both precise (i.e., unbiased) and features small uncertainty in the IOP estimate. This can be achieved by an intraocular pressure measurement arrangement for measuring pressure of an eye of a patient.

An exemplary arrangement includes means for detecting at least one of acoustic reflectivity, optical reflectivity, optical path difference, positioning an intraocular pressure measurement arrangement with respect to the eye, orientation of an intraocular pressure measurement arrangement with respect to the eye, shape of cornea and corneal thickness; at least one source for producing at least one of acoustic, nonlinear acoustic, mechanical and a nonlinear mechanical wave from a distance coupling to the eye of a patient to generate at least one surface wave to the eye; means for triggering data acquisition of the pressure measurement arrangement; means for detecting at least one surface wave from a distance from the eye to extract surface wave information; and means for determining pressure information of the eye based on said surface wave information.

Exemplary embodiments are based on detection of at least one of acoustic reflectivity, optical reflectivity or optical path difference, positioning of intraocular pressure measurement arrangement with respect to the eye, orientation of intraocular pressure measurement arrangement with respect to the eye, shape of cornea and corneal thickness, and on production of at least one of acoustic, nonlinear acoustic, mechanical and a nonlinear mechanical wave from a distance coupling to the eye of the patient to generate at least one surface wave to the eye; and on triggering of data acquisition of the eye pressure measurement arrangement.

Exemplary embodiments enable patient and user friendly use with no need to touch sensitive surfaces of an eye, together with advanced methods to process measurement information in order to extract quantitative pressure information of the eye. One benefit is that disclosed embodiments can be utilized from one patient to another with less risk for contamination as contact to the eye is avoided.

Exemplary embodiments as disclosed herein are based on excitation of acoustic waves into air, which then can couple to an eye of a patient and generate linear or non-linear waves that travel on the surface of the eye. At least one of time-of-flight, speed of sound, attenuation, frequency content, dispersion of these waves or surface motion can then be detected via a single or multiple detector(s). The IOP can then be subsequently determined from these parameters.

The generation of acoustic waves in air can be done in a multitude of ways, most of which involve either a chemical explosion, plasma burst (either mechanically or electrically or optically generated) or a mechanical impact of two surfaces. The combining factor in all of these is the need for energy: all the methods involve large amounts of energy to be released in a short timeframe within a small volume of material. To be commercially viable, this energy storage needs to be safe to the patient and easy to generate by the operator.

In exemplary embodiments according to the present disclosure, non-contacting photoacoustic and ultrasonic intraocular pressure (IOP) measurement techniques are disclosed, which may have for example the following specifications and/or requirements: non-contact excitation and detection methods, which are safe for the patient, determination of essentially accurate intraocular pressure (IOP) values, possibility to follow-up of patient's IOP values, and such techniques can be used by a health care professional and/or by a patient and/or a third person in a convenient and ergonomic way with lowered risk for contamination from patient to patient.

FIG. 1 presents an exemplary embodiment wherein an excitation system for exciting non-linear waves into air includes either one or several solenoids 100a and a weight 101a (e.g. metallic and magnetized or non-magnetized) made out of a magnetic material with rod 104 attached to the weight. The solenoids 100a are used to move the weight-rod system (101a, 104) within the cavity of the solenoid. This rod then impacts on a surface (impacting target 105a) that can be either hard or soft, and the impact between the rod and the surface generates a non-linear wave into air from the other side of the impacting target, i.e. sound emitter 105b. The tip of the rod is optimally shaped (conical, corrugated, grooved, patterned, mathematical function).

Target 105a is a target made out of a material (man-made or natural, hard or soft) with optional surface shaping (conical, corrugated, grooved, patterned, mathematical function) at sound emitter 105b. The solenoids may be timed with a microcontroller, and the timing of the solenoids may be used to adjust the strength and duration of the impact and subsequent non-linear wave generation. The solenoids may be driven with a negative current to allow pullback of the rod-weight system and an inner wall 106 may be used to electromagnetically hold the weight-rod system in place when the device is not in operation to facilitate free orientation of the measurement device.

An exemplary alternative way would be to use the gravity field to hold the weight-rod system. Inner wall 106 may mechanically insulate the two compartments.

A second set of one or several solenoids 100b may be used to drive a counterweight 101b in opposite direction with the primary weight-rod system to reduce the recoil felt by the operator. This can also minimize mechanical crosstalk between the excitation and pick-up parts of the system. Safety walls 102, 103 may be used to prevent weights 101a, 101b from exiting the device. Wall 102 is for example a metallic enclosure with a hole for the rod.

The sound emitter 105b emits an acoustic wave that couples to the eye 109. The wave propagating on the interfaces of the eye is picked up by a vibrometer 107 and an optical beam 108.

The receiving electronics may be triggered by a piezoelectric transducer that can either be attached to the casing of the impactor (102) or that may detect the non-linear wave from afar.

Figure 2:
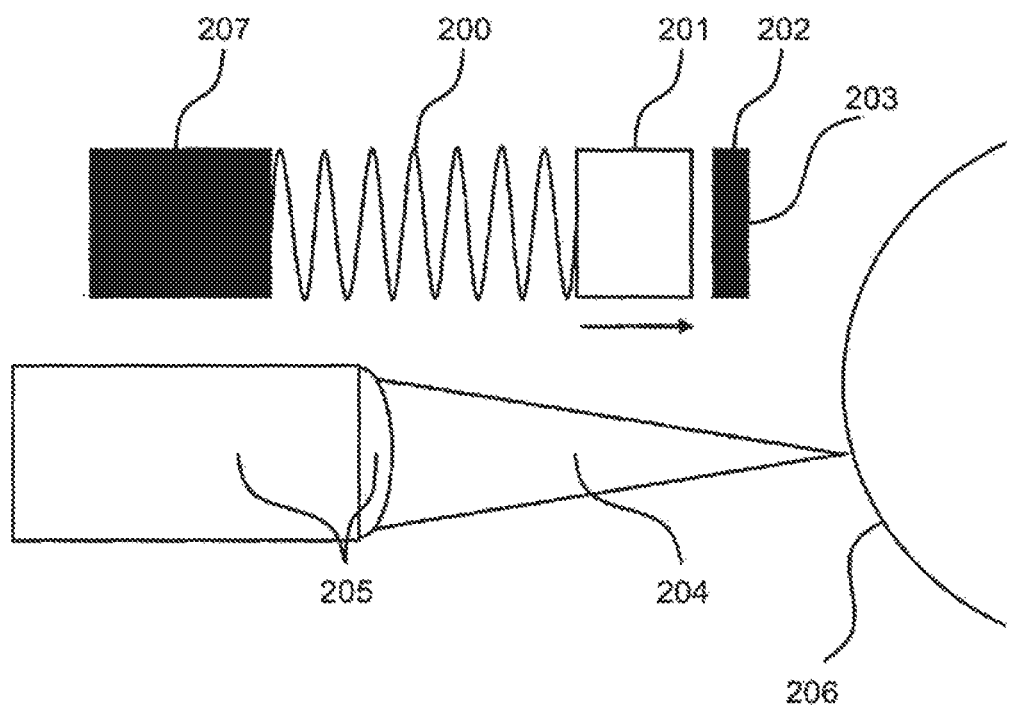
FIG. 2 presents an exemplary embodiment of a measurement arrangement with a spring-loaded impacting device capable of non-linear excitation and optical pickup means.

FIG. 2 presents an exemplary embodiment wherein the spring-driven non-linear wave excitation system includes a rigid structure 207 attached to a spring 200, which moves the weight 201 impacting against a target 202. Sound emitter 203 emits an acoustic wave that is coupled to the eye 206. The wave propagating on the interfaces of the eye is picked up by vibrometer or optical path difference measuring device 205 and optical beam 204.

A rod may be inserted through the weight to allow the operator to arm the device. This weight-spring system may be placed inside a metal casing with a groove and several stopping grooves milled into it. These stopping grooves allow different controlled energy levels to be stored into the spring, and subsequently allow modifying the parameters of the non-linear excitation at release of the stored energy.

Figure 3A:
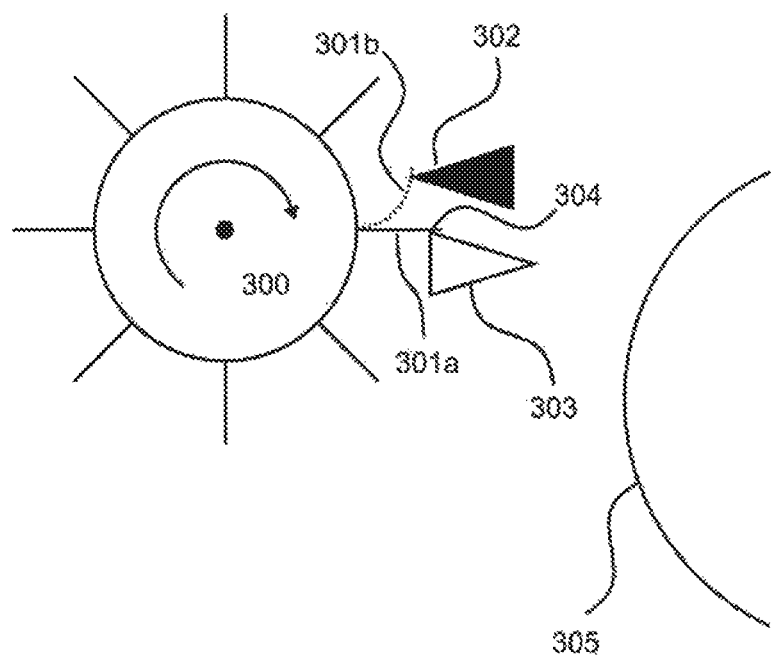
FIGS. 3a-b present an exemplary device capable of non-linear wave excitation based on rotating rods or strips impacting against a target/targets.

FIG. 3a presents an exemplary embodiment of an acoustic wave excitation system which includes a wheel 300 that rotates with rods or strips 301a attached to it near the eye 305. In an exemplary embodiment, these rods or strips 301a are made out of an elastic material and may be armed by rotating them against an arming target 302 made out of a hard material: the rods or strips bend 301b, thus storing energy into them. Once the rods or strips have bent enough, the energy is released by the rod or strip rapidly straightening and impacting against an impacting target 304. The non-linear wave is generated in this impact and emitted from sound emitter 303. The parameters of the non-linear excitation may be altered by adjusting the length and shape of the rods or strips, spacing of the rods or strips, the material of the rods or strips and the rotation speed of the wheel.

Figure 3B:
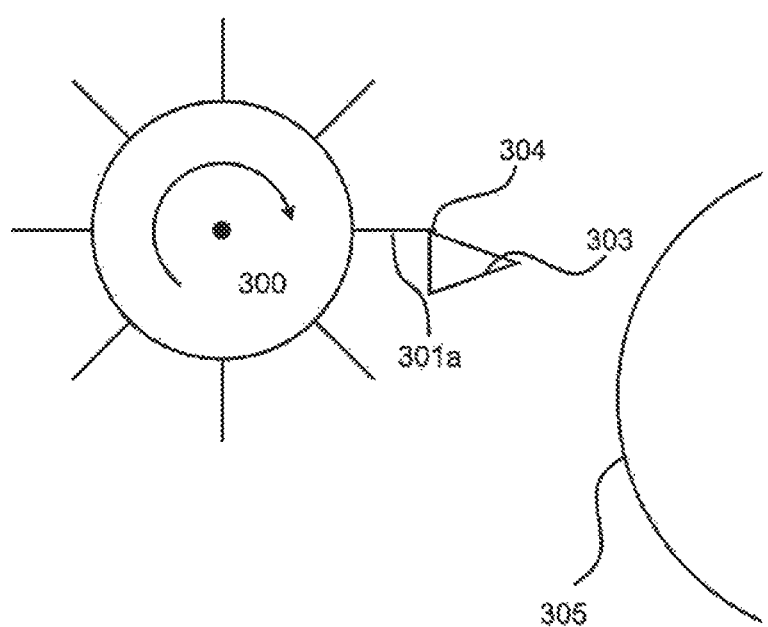

FIG. 3b presents another embodiment in which the wheel 300 rotates with a high angular velocity and rigid rods or strips 301a impact directly against an impacting target 304 and sound is emitted from sound emitter 303 towards the eye 305. In this embodiment, the parameters of the shock wave excitation may be altered by adjusting the rotation speed of the wheel and material of the rods or strip and the target.

Figure 4:
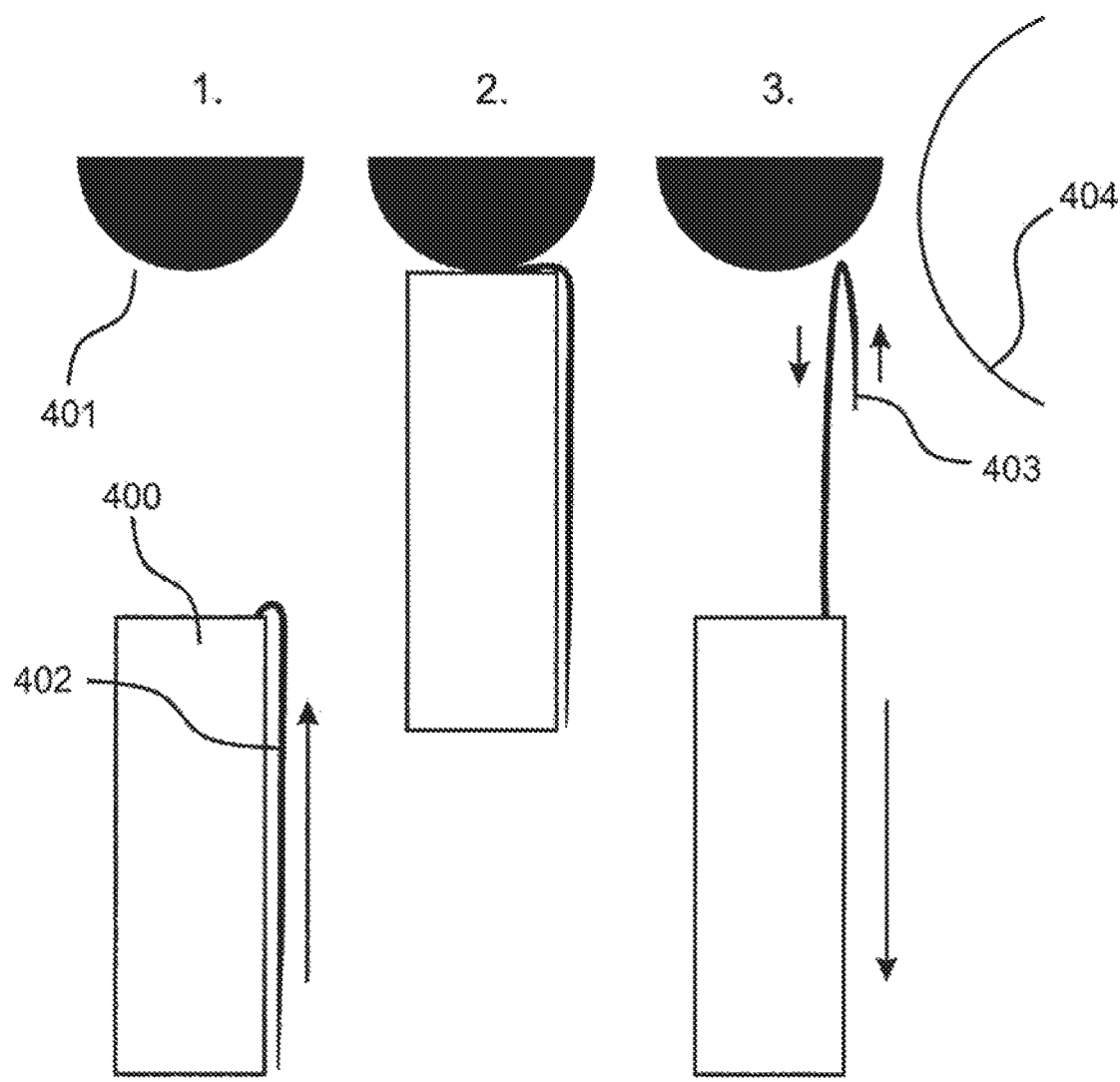
FIG. 4 presents exemplary means for non-linear excitation based on a whiplash effect generating a non-linear wave in air.

FIG. 4 presents an exemplary embodiment of non-linear wave excitation system, located near eye 404, which includes a weight 400 driven by solenoids with an elastic string 402 attached to it (step 1). The weight is rapidly driven against a target 401 (step 2), and the elastic recoil of the weight from the target rapidly changes the movement direction of the weight (step 3). Alternatively a rapid switch in solenoid current reverses the momentum of the weight. This change in the sign of the momentum of the weight causes the elastic string to change its momentum a short amount of time later, resulting in a whiplash-like motion and generation of a non-linear wave in air near the string tip 403. The parameters of the non-linear wave excitation can be altered by adjusting the length or dimensions or material of the string and the movement velocity as a function of time (velocity profile) of the weight.

Figure 5:
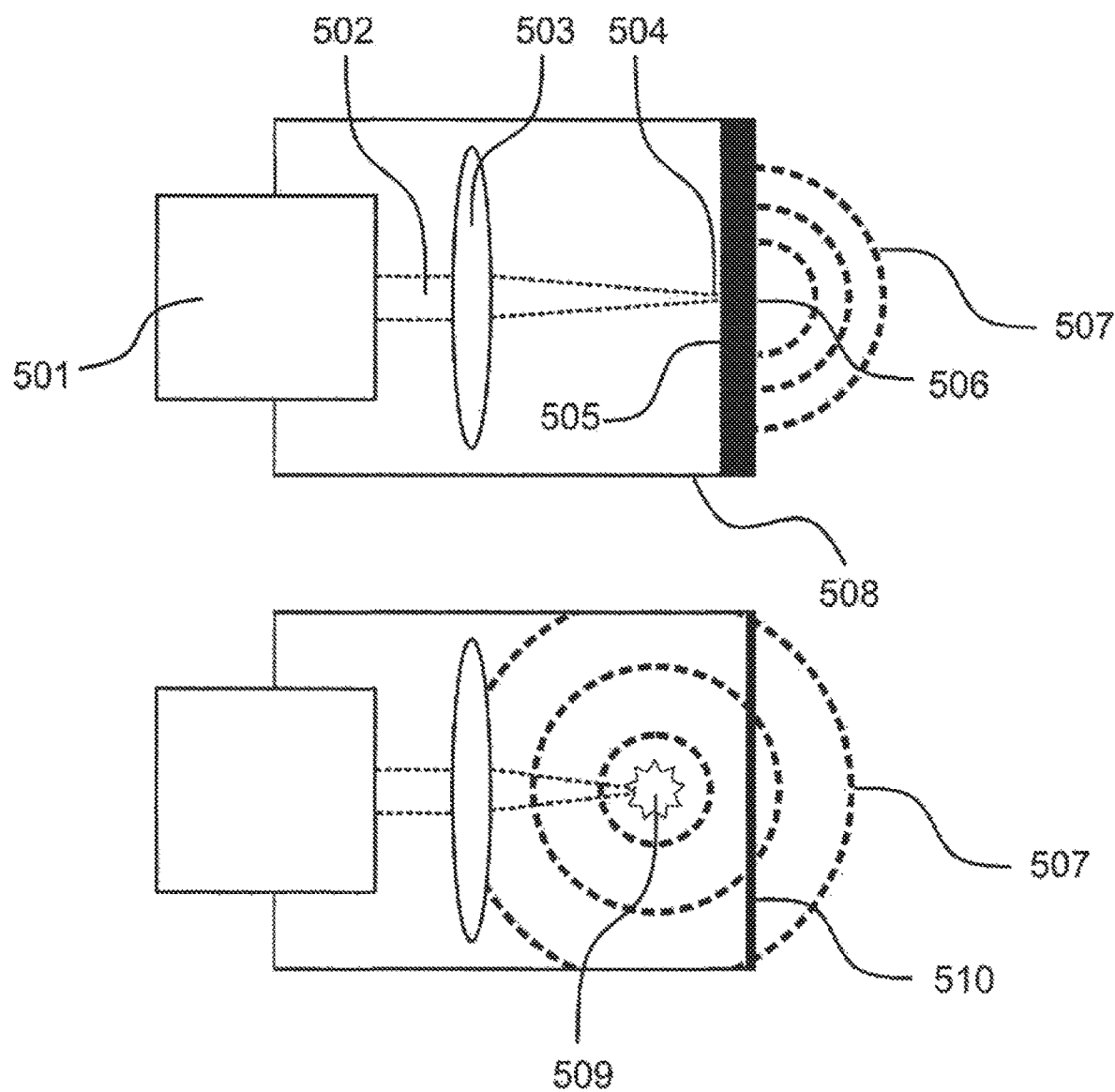
FIG. 5 presents exemplary laser based means for non-linear wave excitation.

FIG. 5 presents an exemplary embodiment in which the laser system 501 generates a laser beam 502 focused by optics 503 onto a point 504 on an optically absorbing target 505. Thermoelastic expansion or ablation of absorbing material 505 generates sound waves 507 that are emitted from the sound emitter 506. Optionally the optics 503 are not required. The embodiment can have walls 508 that prevent light or sound harmful to the patient from escaping the system. Optionally the laser beam can be focused to a point 509 inside material (gas, liquid or solid) to obtain optical breakdown (plasma generation) and generation of sound waves 507. The sound is transmitted through a thin solid membrane or a thin porous membrane or plate 510 that acoustically couples the gas, liquid or solid to the air outside the device.

Figure 6:
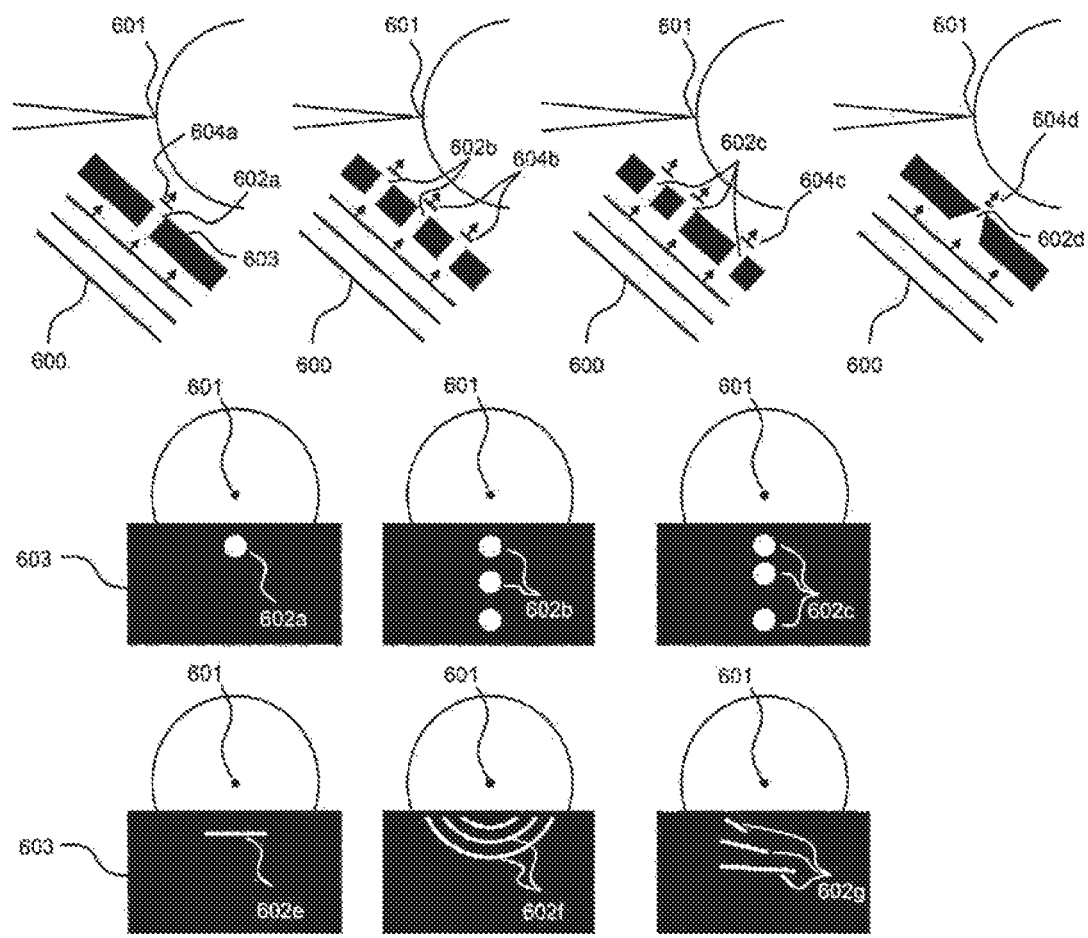
FIG. 6 presents exemplary arrangements to control propagation of excited wave.

FIG. 6 presents an exemplary embodiment according to the present disclosure in which the generated non-linear wavefront 600 may be shaped (604a-604d) with an acoustically reflecting, absorbing, time-delaying, or dispersion removing material 603 with one more many pinholes 602a-602d or slits 602e-602g placed in front of the propagating wavefront. These pinholes or slits may be circular or arbitrary shaped. The pinholes may also converge 602d or diverge towards the eye. The pinholes allow for point-like excitation 602a on the eye surface, and also allow for time-delayed excitation 602b, 602c, and thus shaping the mode propagating on the surface of the eye. Time-delayed excitation or a confocal arrangement of slits 602f, 602g can be used for natural focusing or dispersion removal of the propagating waves into the point of optical detection 601 of the wave on the eye. In addition, this can be used to reduce the effects of interfering modes. The pinhole system in addition eliminates the crosstalk between the excitation and the pickup arising from the non-linear wave propagating in air between the sample and the pickup.

In an exemplary embodiment, a patient may be soothed with a psychologically designed excitation sound pattern in combination with optional soothing light, images or music. This increases the repeatability of the measurement by reducing the stress of the patient and resulting eye movement from the measurement situation.

Figure 7:
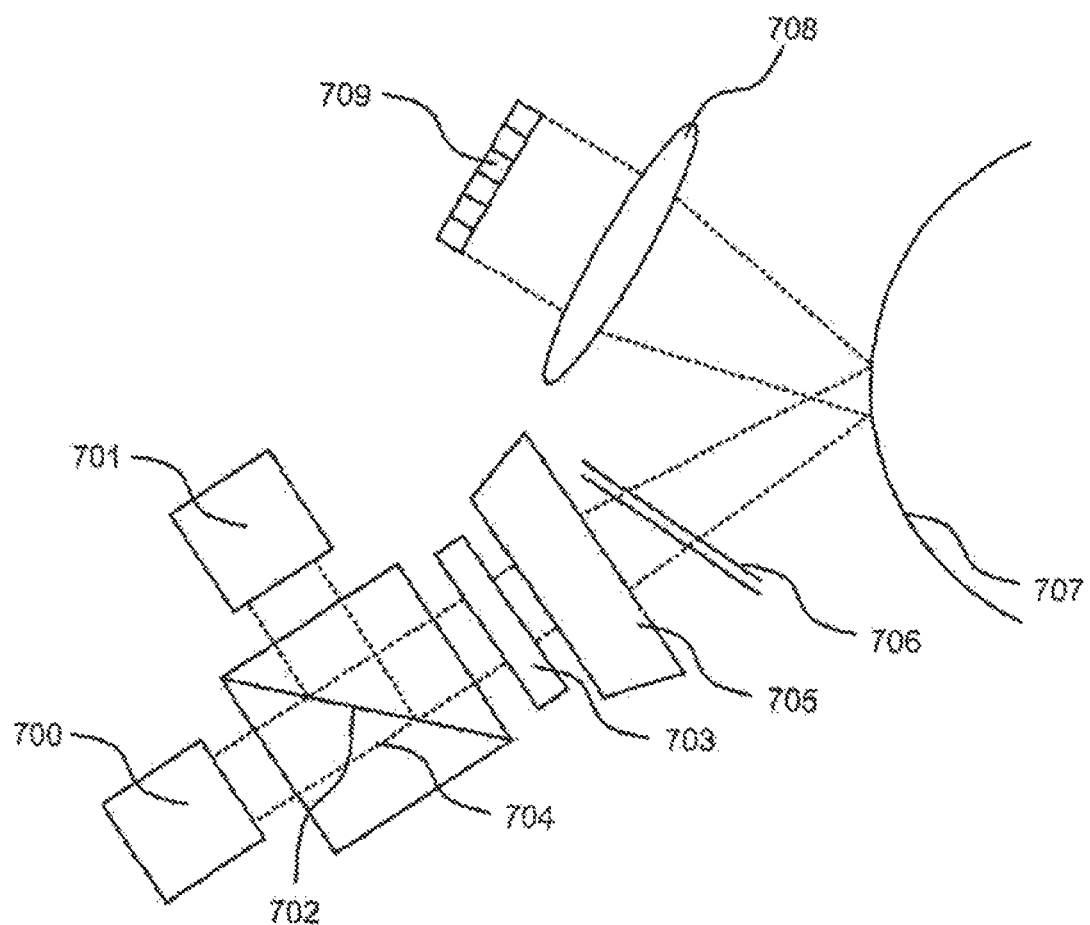
FIG. 7 presents a low power wide beam measuring arrangement.

FIG. 7 presents an exemplary embodiment for detecting corneal surface waves and adjusting tonometer positioning for measurement is using a wide (eg 2-8 mm) output beam of coherent light directed to the cornea and detecting reflected light at an angle. If the beam is directed from the front of the eye, the reflection is measured from one or more positions at different angle. If the beam is directed obliquely to the eye the reflected light is measured from the opposite side. The beam can also be directed and detected from several directions.

The light source can include a laser 700 or lasers 700, 701 or led lights 700, 701 or superluminescent diodes 700, 701 of one or more different wavelengths, wherein beamsplitter 702 or beamsplitters (plate or cubical) direct the beam(s) 704 to the receiving optics. After collimation optics 703 which can include positive or negative lenses, the light beam propagating towards the cornea can be modified with for example beam expander optics 705 comprising of positive or negative lenses in Kepler or Galilean configuration. The light is directed through a diffraction grating (holographic or grooved), etalon or both 706 to form an interference pattern on the surface of the cornea 707. An intraocular pressure measurement arrangement can have as an exemplary means for detecting a receiver having at least three photodetectors in the array 706 and optics (lense or lenses or aspherical) 708 focusing onto or close to the surface of the cornea. Each photo-detector can have its own lens or aperture to enhance the signal and to reduce noise.

Figure 8:
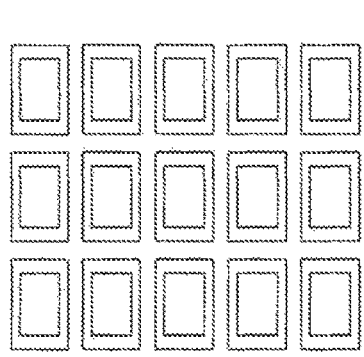
FIG. 8 presents examples of different photodetector arrays.
Figure 8:
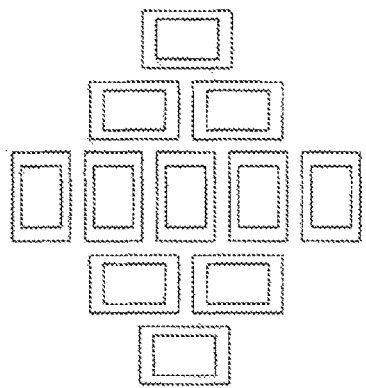
Figure 8:
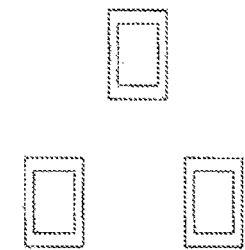

Exemplary photodetector arrangements 800, 801, 802 are presented in FIG. 8. An excitation pressure pulse generated by at least one source (e.g. one or more sources presented in FIGS. 1-5) is transmitted by air to the cornea, generating a surface wave which changes the interference pattern on the corneal surface and the surface wave slightly deflects the cornea forming a local higher-intensity reflection, which both can be observed by the receiver.

An exemplary embodiment can be used in tonometer positioning, i.e. right orientation and measuring distance, by having a light source 700, 701 and receiver 709 with known angles focused on a certain position. The light source is directed towards the cornea 707 and receiver is in position to detect the reflected beam from the cornea. When the light source 700, 701 and receiver 709 are positioned in such way that the center of the detector array 709 records maximum intensity, the tonometer is correctly positioned in distance and orientation. In an exemplary embodiment, the photodetector array includes (e.g., consists of) only three photodetectors 802. Here, the correct position is achieved when all photodetectors have the same or nearly the same signal intensity. Vertical positioning can be achieved by an accelometer or several accelometers aimed along different axis. A gyroscope can be used in detecting circular movement of the tonometer. These sensors can also be used in detecting tonometer movement changes (circular or directional). The measurement can be started when the tonometer is in right position and not moving or when the movement is minimal. A tonometer software can instruct the user to position the tonometer correctly by for example using arrow symbols in a display.

Figure 9:
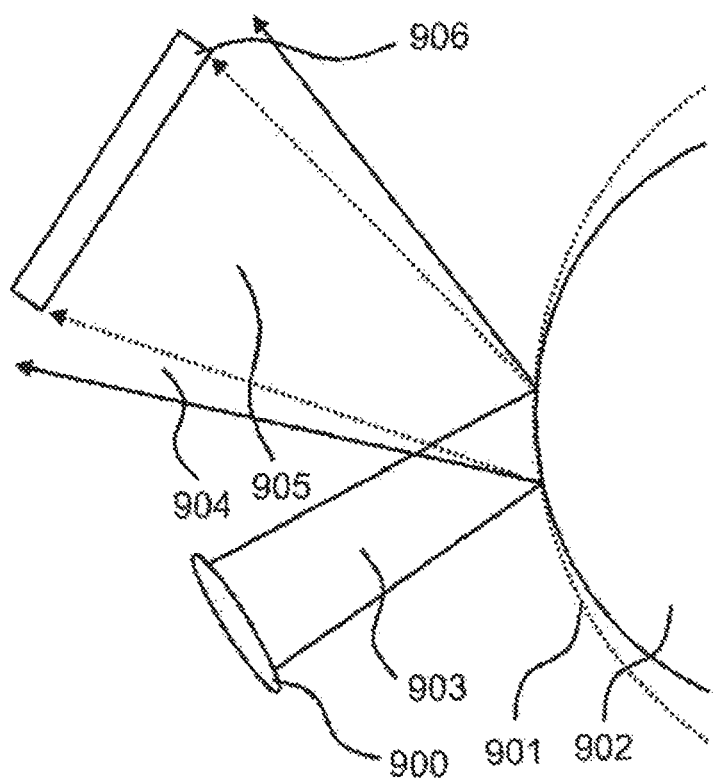
FIG. 9 presents a wide exemplary beam arrangement's capability to measure corneal shape and/or curvature.

FIG. 9 presents an exemplary embodiment where corneal curvature 901, 902 can be evaluated according to how the central and lateral photodiode signal 906 intensity differ from each other, and in case of at least three detectors, from the total signal intensity of reflected light from the cornea. If the corneal radius is small and the corneal curvature is steep, the reflected beam 904, 905 expands more and received signals of central photodetectors differ more from received signals of peripheral photodetectors in the detector array than in the case of larger corneal radius with less curvature.

The measurement system measures the surface disturbances of the corneal surface and surface waves. The receiver has detector array and the detected waves arrive at different times to each of the detector elements. Thus, the surface-wave velocity can be calculated.

Figure 10:
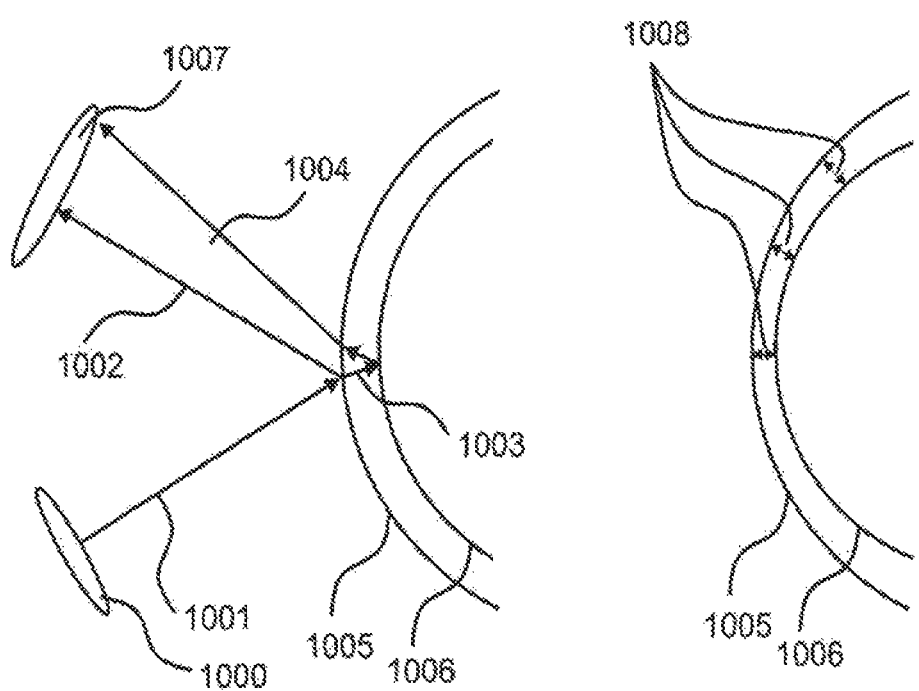
FIG. 10 presents a different path and angle of a reflected lightbeam from front and rear surfaces of a cornea, which can be used in determining a thickness of the cornea.

FIG. 10 presents measurement of corneal thickness. Optics (1000) guide the beam of light to the corneal surface (1001). The reflected light (1001) from the front surface (1005) of the cornea differs in angle from the bundle of the light reflected (1004) from the back of the corneal surface (1003), because of the corneal thickness and the inner portion is steeper in the curvature than the outside surface. Also the difference in refractive index bends the light. Detection optics (1007) including lenses of spherical or aspherical type (1007) guide the light to the detectors. The difference in the reflected angles (1002, 1004) depends of the corneal thickness and is detected by the photodetectors. Thickness may vary with the position along the cornea (1008) and can be measured by means of multiple detectors described before or by moving the detection system along the cornea. This allows detection of possible stress fields in the cornea.

The reflected light from the front surface of the cornea differs in angle from the bundle of the light reflected from the back of the corneal surface, because of the corneal thickness and the inner portion is steeper in the curvature than the outside surface.

When the corneal surface wave moves, photo-detector elements in the array of the receiver receive the rays reflected from the outside and inside surface of the cornea at different times. If the wave is moving from the receiver to the light source, the light ray reflected from corneal outside surface arrives first and after that the light rays reflected from the rear surface of the cornea. Otherwise, on the contrary, a rear portion of the reflected wave is first detected.

When corneal curvature and surface wave velocity are known the corneal thickness can be calculated based on the measurement data. If more than one wavelength is used in measurement, the accuracy can be improved. Different wavelengths have different properties of refraction. Refraction is the change in direction of propagation of a wave due to a change in its transmission medium. The medium changes when entering the cornea, is different inside the cornea, and when exiting the cornea, causing different wavelengths to differ in corneal rear surface reflected light.

Using multi-wavelength coherent light beams which have different refracting properties it is possible to measure the disparity between the surface and the rear wall arrival of the different wavelength beams. In this way more parameters are obtained in solving the equation central to calculating the corneal thickness. Thus, the measurement accuracy is improved.

In exemplary embodiments according to the present disclosure the generated non-linear wavefront can be shaped by a pinhole or a wedge or a patterned surface or a waveguide to allow more localized and coherent linear wave excitation on the eye surface. The pinholes can be shaped to allow larger or smaller cones or other topological shapes (e.g. exponential horns) of non-linear waves to pass through. In addition, the pinholes may be shaped in an arc-like pattern which allows natural focusing of the waves on the eye surface. To reduce the mechanical cross-talk between the excitation and the pickup, the excitation part may be suspended in air with impact absorbing springs or acoustic damping material, e.g. foam or rubber. For positioning of the measuring head, a holographic diffraction grating can be used to project a rectangular grid on the eye surface. A camera mounted on the measuring head images the reflected image of the grid. Based on the distortion of the image of the grid, corneal surface curvature and position relative to the eye (distance, angular tilt) can be calculated. Based on the position data, the measurement head may be moved with a linear stage (piezo or a linear motor) for more precise orientation of the measurement head and to compensate for movement of the operator's hand or the subject's eye.

Figure 11:
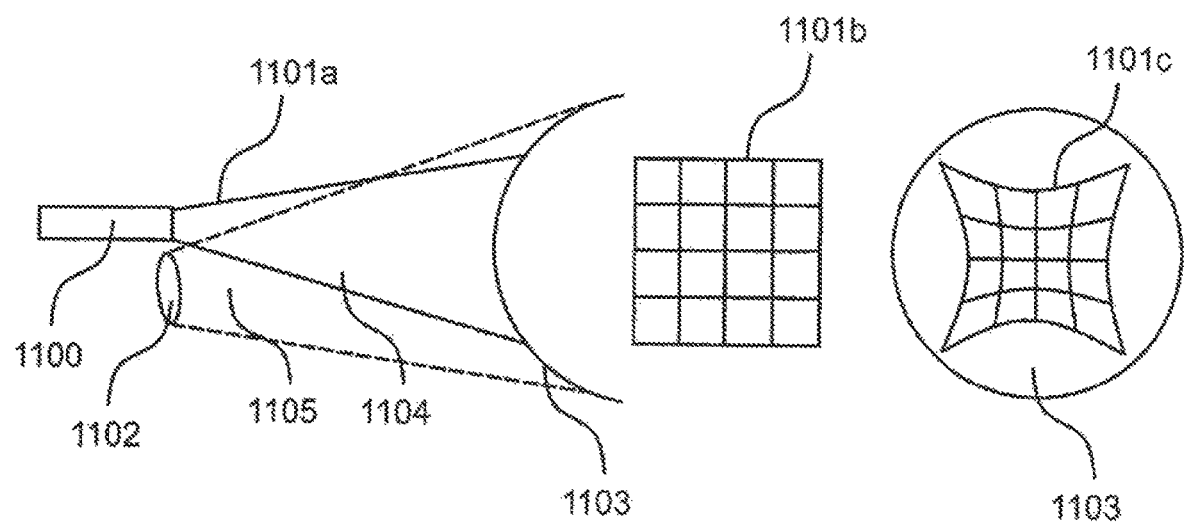
FIG. 11 presents exemplary means for detecting the position and orientation of the measurement arrangement.

FIG. 11 presents exemplary means to detect the measurement arrangement position and orientation. Laser light source 1100 of visible or infrared wavelength incorporating a holographic grid projects 1101a an image of a grid 1101b on the surface of the cornea 1103. The grid is detected with a camera 1102 focused on the surface of the eye. The grid may include (e.g., consist of) any pattern of regular geometric shapes, such as squares. Depending on the position of the measurement arrangement with respect to the eye, the projected holographic grid is distorted 1101c, and from the distortion, the position and orientation of the measurement arrangement can be calculated.

Figure 12:
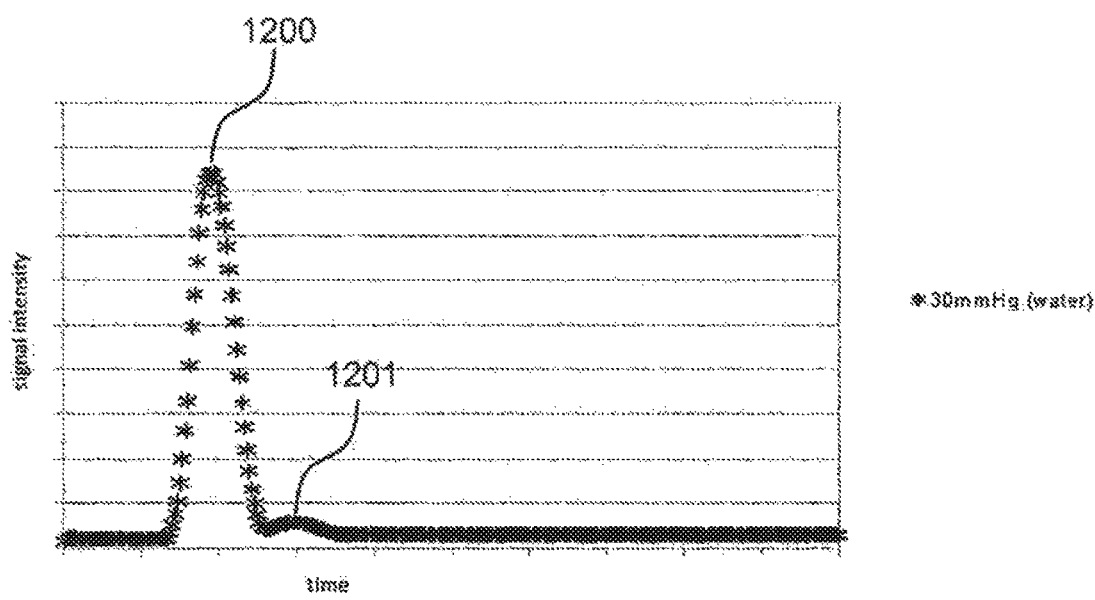
FIG. 12 presents an example of a signal obtained by one photodetector element in array, used in determining corneal thickness.

FIG. 12 presents a preliminary set of data measured with an exemplary arrangement presented in FIG. 10. Two distinct features can be seen: A first arrival reflected from corneal front surface 1200 followed by a smaller wavecrest 1201 which arise from the bottom surface of the cornea.

An exemplary intraocular pressure measurement arrangement according to the present disclosure for measuring pressure of an eye 202 of a patient can include means for detecting one or more of following: acoustic reflectivity, optical reflectivity, optical path difference, positioning of intraocular pressure measurement arrangement with respect to the eye, orientation of intraocular pressure measurement arrangement with respect to the eye, shape of cornea and corneal thickness. The arrangement can include at least one source for producing one or more of the following: acoustic, nonlinear acoustic, mechanical and a nonlinear mechanical wave from a distance 200 coupling to the eye 202 of the patient to generate at least one surface wave to the eye. The measurement arrangement according to the present disclosure can further include means (e.g., a computer processor) for triggering data acquisition of the pressure measurement arrangement. At least one surface wave is detected from a distance 201 from the eye 202 by means for detecting to extract surface wave information, and pressure information of the eye can be determined based on the surface wave information by means for determining pressure information of the eye.

In different kinds of exemplary embodiments according to the present disclosure the measurement arrangement can include one or more of the following: means for non-linear wave generation to the eye 202, means for linear wave pick-up from the eye 202, means for shaping non-linear waves, means for low power wide beam measuring, means for obtaining corneal curvature information, means for obtaining corneal thickness information, and means for determining location and orientation of the measurement arrangement and curvature of the cornea.

In an exemplary embodiment according to the present disclosure the measurement arrangement can include means for triggering in order to calm the patient to reduce measurement spread, and to increase compliance and referrals to other people. Also light and images can be utilized in order to calm the patient for one or more of the purposes.

Next is provided a further description of exemplary FIGS. 1-12. In FIG. 1 is presented exemplary means for non-linear wave generation to the eye 202 and linear wave pick-up from the eye 202, said means including for example: (100)

coils that drive the impacting device, (101*a*) metallic (magnetized or non-magnetized) weight with a (104) rod or strip with optional surface shaping (conical, corrugated, grooved, patterned, mathematical function) attached with a (101*b*) counterweight to reduce the recoil felt by the operator from the excitation. A metallic enclosure (102) with a hole for the rod, a back wall (103) and an mechanically insulating (106) inner wall separating the two compartments are included. A target (105*a*) made out of a material (man-made or natural, hard or soft) with an (105*b*) optional surface shaping (conical, corrugated, grooved, patterned, mathematical function is included). An optical means (107) transmitting and receiving a laser or light beam (108) for surface wave pick-up from the (109) eye is also included.

FIG. 2 presents another exemplary means for non-linear wave generation to the eye 202 and linear wave pickup from the eye 202, said means including: a spring (200) is attached to a solid frame (207) and an (201) impacting mass with either a flat or shaped (conical, corrugated, grooved, patterned) surface. This impacting mass hits the (202) solid target. The (203) solid target surface can be shaped (conical, corrugated, grooved, patterned, mathematical function). The generated non-linear wave travels then through air to the surface of the (206) eye, from where it is picked up by (205) optical means for transmitting and receiving a laser or a light beam (204) (e.g., laser and laser light detector).

FIG. 3 presents another exemplary means for non-linear wave generation to the eye 202, the means including: a wheel (300) with protruding elastic or stiff rods or strips (301*a*) attached to it for rotation. The (301*a*) rods or strips may be either smooth or their (304) surface can be shaped (corrugated, grooved, patterned, mathematical function). When rotating, the wheel makes tension in the rods which press against (302) an arming target (FIG. 3*a*), which makes the rods or strips gather potential energy in the form of spring tension (301*b*). The rod or strip is then released due to the wheel rotation, causing an impact against the (304) impacting target, whose surface may be flat or patterned. The non-linear wave generated then travels to the eye (305). In one alternative embodiment (FIG. 3*b*), the wheel (300) rotates at a high angular velocity, and the (301*a*) rods or strips impact directly against the (304) impacting target, whose surface (303) can be shaped.

FIG. 4 presents another exemplary means for non-linear wave generation to the eye, the means including: a weight 400, displaced by driving means having either a solenoid or a linear motor or by gravitational force or by pneumatic pressure or by an chemical reaction, hits against an elastic impacting target (401). After the impact, an elastic string (402) lags behind due to Newton's 2nd law and generates a whip-like motion (403), which causes localized supersonic displacement and a subsequent non-linear wave which then couples to the eye (404).

FIG. 5 presents another exemplary means for non-linear wave generation, the means including: a laser light source (501) which transmits a laser beam (502) through focusing optics (503). In an exemplary embodiment, the laser beam is focused (504) on the surface of a target (505), made out of natural or synthetic materials, such as metal. The other surface of the target (506) emits a non-linear wave (507). In another embodiment, the laser beam (502) is focused in a spot in the medium (air, water, solid) it travels in (509), and generates an optical breakdown (plasma) which transmits the generated non-linear wave (507) through a membrane (510).

FIG. 6 presents an exemplary embodiment according to the present disclosure in which the generated non-linear wavefront 600 can be shaped (604*a*-604*d*) by using means for shaping non-linear waves, the means including for example: an acoustically reflecting, absorbing, time-delaying, and/or dispersion removing material 603 with one more many pinholes 602*a*-602*d* and/or slits 602*e*-602*g* placed in front of the propagating wavefront. These pinholes or slits may be circular or arbitrary shaped. The pinholes may also converge 602*d* or diverge towards the eye. The pinholes allow for point-like excitation 602*a* on the eye surface, and also allow for time-delayed excitation 602*b*, 602*c*, and thus shaping the mode propagating on the surface of the eye. Time-delayed excitation or a confocal arrangement of slits 602*f*, 602*g* can be used for natural focusing or dispersion removal of the propagating waves into the point of optical detection 601 of the wave on the eye. In addition, this can be used to reduce the effects of interfering modes. The pinhole system in addition eliminates the crosstalk between the excitation and the pickup arising from the non-linear wave propagating in air between the sample and the pickup.

FIG. 7 presents exemplary means for low power wide beam measuring, the means including a laser or lasers of one or more different wavelengths and/or LED lights (700, 701) of one or more different wavelengths, optics and beamsplitters (702) in order to direct the beams (704) to the optics. The optics can include a collimator (703) and beam expanding optics (705). In an exemplary embodiment, an etalon or a diffraction grating (706) can be used to form an interference pattern on the surface of the cornea (707). The reflected light is then collected through receiving optics (708) and recorded with a photodiode array (709). Each photodiode may have its own lens or aperture to improve the signal-to-noise ratio.

FIG. 8 presents an example of a detecting means having a photodetector array configuration including (e.g., consisting of) 15 elements (800), 11 elements (801) and 3 elements (802). Photodiodes may be positioned in a rectangular, spherical or irregular grid pattern.

FIG. 9 presents exemplary means for obtaining corneal curvature information by evaluating the corneal curvature, for example, according to how the central and lateral photodetector signal intensity differ from each other, and in case of three detectors or also more, the total signal intensity of reflected light from cornea. A light source (900) emits a beam of light (903) which reflects from the surface of the cornea. If the corneal radius is small (902) and the corneal curvature is steep, the reflected beam expands more (904) and central photodetectors received signals (905) differ more from peripheral photodetectors in the detector array (906) than in the case of larger corneal radius (901) with less curvature.

FIG. 10 presents exemplary means for obtaining the corneal thickness information and/or information on waves travelling on the cornea. The reflected light from the front surface of the cornea (1002) travels through the cornea and differs in angle from the bundle of the light reflected from the back of the corneal surface (1003), because the corneal thickness and the inner portion (1006) is smaller in curvature than the outside surface (1005). A photodetector array (1007) detects the location of the reflected beam. The differences in the corneal thickness (1008) as a function of location can be inferred from the angle if the corneal shape is known.

FIG. 11 presents exemplary means for determining the location and the orientation of the measurement arrangement and the curvature of the cornea, the means including: a light source (1100) incorporating a holographic diffraction grating projects (1101*a*) a rectangular grid (1101*b*) on the surface of the cornea (1103). This projected light (1104) is reflected (1105) from the surface and is detected with a camera (1102). From the distorted image of the grid (1101c), the curvature of the cornea is calculated (e.g., by a computer processor) if the projector (1100) location and orientation is known. The distance between the projector (1100) and the cornea surface (1103) may be determined from the apparent size of the grid.

FIG. 12 presents a sample of the signal obtained. Activation (e.g. impactor/spark) excitation is created, which arrives to the cornea forming a surface wave. The corneal surface waves can be detected by photo-detectors, which can measure the surface disturbances of the corneal surface and surface waves. The receiver can have a detector array and the detected waves can have arrived at different times to each of the detector elements. Thus, the surface-wave velocity can be calculated. A light bundle reflected from the outside surface (1201) of the moving surface wave arrives first to the detector element and after that the light bundle reflected from corneal inside surface (1202) arrives. The beams reflected from the rear of the cornea are of lower intensity than reflection from front surface.

On the basis of the present disclosure an ideal tonometer can be implemented, capable of measuring intraocular pressure with fast comfortable measurements without anesthetic and disposable waste and operated by an unskilled operator.

Although embodiments the invention have been presented in reference to the attached figures and specification, the invention is by no means limited to those, as the invention is subject to variations within the scope allowed for by the claims.

Thus, it will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

The invention claimed is:

1. An intraocular pressure measurement arrangement for measuring eye pressure, the arrangement comprising:
   at least one source configured to produce an excitation pressure pulse formed by nonlinear waves in which a principle of superposition does not hold, and transmitted by air to a surface of an eye to generate at least one surface wave for an eye measurement;
   a detector configured to detect, based on light reflected off the eye, the at least one surface wave at a distance from the surface for extracting surface wave information; and
   one or more processors configured to determine the eye pressure based on said surface wave information.

2. The intraocular pressure measurement arrangement according to claim 1, wherein the detector configured to detect the at least one surface wave comprises:
   one or more devices configured to determine the velocity of the surface wave.

3. The intraocular pressure measurement arrangement according to claim 1, wherein the detector configured to detect the at least one surface wave comprises:
   one or more processing devices configured to determine changes, caused by the surface wave, in a light-interference pattern on a corneal eye surface.

4. The intraocular pressure measurement arrangement according to claim 1, further comprising:
   means for linear wave pick-up.

5. The intraocular pressure measurement arrangement according to claim 1, further comprising:
   means for shaping the nonlinear waves.

6. The intraocular pressure measurement arrangement according to claim 1, further comprising:
   a measurement system configured to measure the surface wave with a 2-8 mm wide measurement beam.

7. The intraocular pressure measurement arrangement according to claim 1, further comprising:
   means for obtaining corneal curvature information.

8. The intraocular pressure measurement arrangement according to claim 1, further comprising:
   means for obtaining corneal thickness information.

9. The intraocular pressure measurement arrangement according to claim 1, further comprising:
   one or more processors configured to determine curvature of a cornea.

10. An intraocular pressure measurement method for measuring eye pressure, the method comprising:
    producing an excitation pressure pulse formed by nonlinear waves in which a principle of superposition does not hold, and transmitted by air to a surface of an eye to generate at least one surface wave for an eye measurement;
    detecting, based on light reflected off the eye, at least one surface wave at a distance from the surface to extract eye surface wave information; and
    determining the eye pressure based on said surface wave information.

11. The intraocular pressure measurement method according to claim 10, further comprising:
    determining the velocity of the surface wave.

12. The intraocular pressure measurement method according to claim 10, further comprising:
    determining changes, caused by the surface wave, in a light-interference pattern on a corneal eye surface.

13. The intraocular pressure measurement method according to claim 10, further comprising:
    conducting a linear wave pick-up.

14. The intraocular pressure measurement method according to claim 10, further comprising:
    shaping the non-linear waves.

15. The intraocular pressure measurement method according to claim 10, further comprising:
    measuring the surface wave with a 2-8 mm wide measurement beam.

16. The intraocular pressure measurement method according to claim 10, further comprising:
    obtaining corneal curvature information.

17. The intraocular pressure measurement method according to claim 10, further comprising:
    obtaining corneal thickness information.

18. The intraocular pressure measurement method according to claim 10, further comprising:
    determining curvature of a cornea.

19. An intraocular pressure measurement arrangement for measuring eye pressure, the arrangement comprising:
    at least one source configured to produce an excitation pressure pulse formed by nonlinear waves in which a principle of superposition does not hold, and transmitted by air to a surface of an eye to generate at least one surface wave for an eye measurement;

a detector configured to detect, based on light reflected off the eye, the at least one surface wave at a distance from the surface to extract surface wave information; and one or more processors configured to determine an eye pressure based on said surface wave information.

\* \* \* \* \*